United States Patent [19]

Urakami

[11] Patent Number: 4,880,415
[45] Date of Patent: Nov. 14, 1989

[54] WARM BATH FOR HANDS AND FEET

[76] Inventor: Hideaki Urakami, 6-18, Hibarigaoka 1-chome, Takarazuka-shi, Hyogo 665, Japan

[21] Appl. No.: 160,604

[22] PCT Filed: May 2, 1986

[86] PCT No.: PCT/JP86/00230
§ 371 Date: Dec. 22, 1987
§ 102(e) Date: Dec. 22, 1987

[87] PCT Pub. No.: WO87/06454
PCT Pub. Date: Nov. 5, 1987

[51] Int. Cl.[4] .............................................. A61F 7/00
[52] U.S. Cl. .................................... 604/291; 128/365; 128/370
[58] Field of Search .................. 604/289, 291; 128/65, 128/365, 369, 370, 400

[56] References Cited

U.S. PATENT DOCUMENTS

| 1,842,192 | 1/1932 | Patterson | 128/370 |
| 3,942,515 | 3/1976 | Servos et al. | 128/746 |
| 4,149,536 | 4/1979 | Villard | 128/365 |
| 4,298,006 | 11/1981 | Parks | 128/399 |
| 4,513,735 | 4/1985 | Friedson et al. | 128/65 |
| 4,632,115 | 12/1986 | Bernardini | 128/370 |
| 4,696,303 | 9/1987 | Bernardini | 128/370 |

FOREIGN PATENT DOCUMENTS

| 60-163926 | 10/1985 | Japan. | |
| 61-10739 | 1/1986 | Japan. | |
| 457892 | 12/1936 | United Kingdom | 126/65 |

OTHER PUBLICATIONS

A Thermostatic System for Biomedical Applications, 1/1975.
System of Physiologic Therapeutics, Winternitz, Wihelm, 1902, 398–400.

Primary Examiner—C. Fred Rosenbaum
Assistant Examiner—Mark O. Polutta
Attorney, Agent, or Firm—Jordan and Hamburg

[57] ABSTRACT

A warm bath for simultaneously soaking and warming the hands and feet in a bathing agent consisting mainly of wax includes an upper and lower container each containing the bathing agent, the upper and lower container each having a bottom wall and a peripheral side wall which is generally upright. The bottom wall and peripheral side wall of each container comprises a base structure and an inner layer on the base structure, the inner layer being made of a corrosion-resistant material. The base structure has a bottom outer surface juxtaposed to the bottom wall and a side outer surface juxtaposed to the side wall. A first electric heater is provided on the bottom outer surface and a second electric heater is provided on the side outer surface. A temperature sensor for detecting the temperature of the bathing agent is provided in each of the containers, and a temperature control is operably connected between the temperature sensor and the first and second electric heaters for controlling the temperature of the bathing agent in each of the containers, whereby the entire volume of the bathing agent in each of the upper and lower containers is uniformly heated by the first and second electric heaters and the temperature of the bathing agent in the upper and lower containers is maintained substantially even at all locations in the respective container by the first and second electric heaters.

9 Claims, 5 Drawing Sheets

FIG.7

WARM BATH FOR HANDS AND FEET

FIELD OF THE INVENTION

The present invention relates to a warm bath for hands and feet used for warming the hands and feet by soaking them in a warm molten bathing agent consisting mainly of a wax.

BACKGROUND OF THE INVENTION

It is well known that a hot spring, in particular a mineral spring, therapy is very effective for recovering from fatigue, soothing muscular fatigue and pain, accelerating circulation of the blood, slimming fatness and activating internal organs and so on. This therapy is designed to warm the body by the warm water and to accelerate warming operation of the body by absorbing mineral ions contained in warm water, thereby stimulating cells in the body and accelerating perspiration to improve metabolism.

However, hot spring therapy involves difficulty such as as requiring a patient to visit a hot spring or such disadvantage as causing a heavy burden to the heart or other parts of the body, because of soaking the entire body in a bath. When conducting the therapy, therefore, there is not only a possibility to fatigue the body, but it is also not suitable to those who have heart disease or high blood pressure.

In order to avoid such problems, the inventor has some time ago developed a novel apparatus for applying a warm bath therapy to those who have heart disease or the like with ease at home, together with a bathing agent used therein and consisting mainly of a wax containing minerals. The warm bath and the bathing agent are for partly warming the hands and feet soaked in the bath filled with the warm molten bathing agent to realize the body warming effect, which is as good as the body bathing of hot spring therapy.

According to the experiment carried out by the inventor, however, when soaking the hands and feet in the bath, sweat and secretions are excreted from the body to erode the inner surface of the bath since such sweat and secretions are acid. As a result, the bath becomes unusable due to deterioration.

In addition, according to the experiment carried out by the inventor, since the bathing agent consists mainly of the wax, when it is warmed and molten, convection is not performed sufficiently inside the bath due to its viscosity. Therefore, the bathing agent temperature in the bath is not even and its precise control is difficult, resulting in such problems as scalding the hands and feet when they are soaked in a hot temperature portion, or solidifying the bathing agent at a colder portion to make the soaking difficult.

It is an object of the present invention to provide a warm bath for hands and feet, which solves the above problems at once by devising a structure of the bath in which the bathing agent is filled, and by providing an arrangement of the heating portion for heating the bath.

DISCLOSURE OF THE INVENTION

A warm bath for hands and feet of the present invention designed to warm the hands and feet soaked in a warm molten bathing agent consisting mainly of a wax, includes a bath having a pair of containers arranged in upper and lower stages for filling with the bathing agent, a heating portion for heating each container disposed in the bath, a sensor for detecting the temperature of the warm molten bathing agent, and a temperature control for controlling the operation of the heating portion corresponding to the result detected.

In the warm bath for hands and feet of the present invention, each container of the bath is formed with a corrosion-resisting layer on the inner surface.

In addition, in the warm bath for hands and feet of the present invention, the heating portion is divided into a first heating portion and a second heating portion, the former being disposed similarly on the bottom of each container and the latter being disposed similarly on the periphery thereof.

According to the present invention, when the bathing agent is heated and molten in the bath and the hands and feet are soaked thereinto, a warming effect as good as body bathing of hot spring therapy can be obtained, and at the same time, recovering of fatigue, soothing of the muscular fatigue and pain, acceleration of the blood circulation, slimming of the fatness and activation of organic functions and the like can be accomplished without stressing various parts of the body including the heart as occurred in body bathing. Besides, a strong thermal stimulus is given simultaneously to the hands and feet studded with a plurality of meridian points, which is as efficacious as a moxibustion, and at the same time, by partially destroying a film of wax formed on the soaked hands and feet to resoak, a strong thermal stimulus can be applied locally repeatedly, resulting in an effective therapy of the affected parts. Moreover, waste materials in the body are excreted from the gaps between nails of the hands and feet to accelerate the metabolism, so that it is contributive for promoting the health of all people.

Since a corrosion-resisting layer is formed on the inner surface of each container forming the bath, even if acid sweat and secretions are excreted into these containers from the body, the inner surface of the container is resistant to corrosion, thereby durability of the bath and safety of the apparatus can be considerably improved.

Moreover, the heating portion is divided into a first and second heating portions, the former being disposed equivalently on the bottom of each container and the latter being disposed equivalently on the periphery thereof, so that even if circulation inside the bath is hindered by the viscosity of the bathing agent, the warm molten bathing agent temperature in the bath is uniform and not only the temperature can be controlled precisely, but also such problems as scalding of the hands and feet by the hot temperature portion or hindering the soaking of hands and feet by the solidified bathing agent in the colder portion can be totally avoided.

BEST MODE FOR CARRYING OUT THE INVENTION

Figure 1:
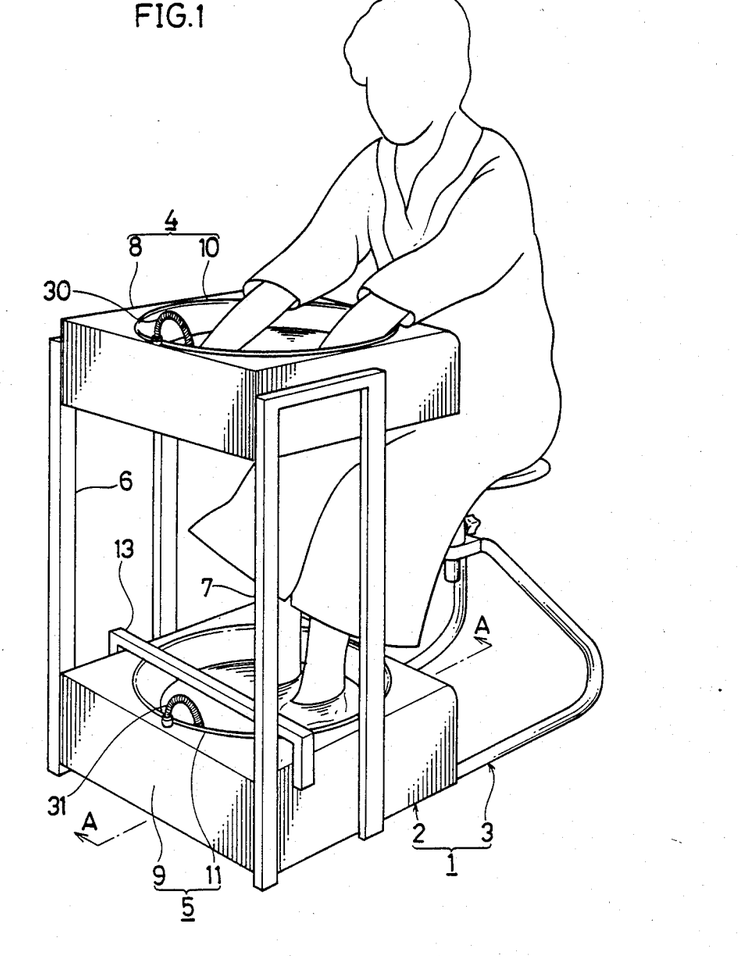
FIG. 1 is a perspective view showing a general structure of a warm bath for hands and feet in accordance with one embodiment of the present invention.
Figure 2:
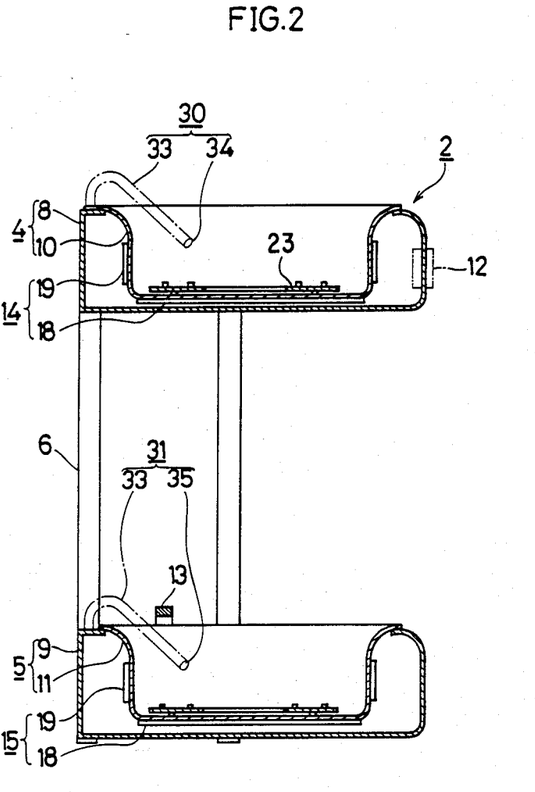
FIG. 2 is a vertical sectional view of an apparatus taken along the line A—A of FIG. 1.

FIGS. 1 and 2 show a warm bath for hands and feet 1 in accordance with one embodiment of the present invention, wherein the external and sectional views of the apparatus are respectively shown.

The apparatus 1 in the drawing comprises a body 2 including an upper bath 4 for soaking the hands and a lower bath 5 for soaking the feet, and a chair 3 coupled to the front position of the body 2.

The upper bath 4 and the lower bath 5 are supported in parallel vertically in two stages between two side frames 6, 7, and are both provided with containers 10, 11 having an upper openings on the upper surface of box type bodies 8, 9. In front of the body 8 of the upper bath 4, a control panel 12 having a power switch and a temperature adjusting knob and the like (not shown) is disposed, and on the body 9 of the lower bath 5, a foot rest 13 is arranged horizontally.

In the bodies 8, 9 of each bath 4, 5, heaters 14, 15 for heating the containers 10, 11 are disposed respectively, thereby a bathing agent filled within each container 10, 11 is heated and molten.

The heating agent is consisting mainly of a wax, into which less than 1% by weight of minerals is added and if necessary, vitamins such as vitamin E and P, an antiphlogistic such as methyl salicylate and an anodyne such as 1-menthol are added. In the embodiment, though a paraffin wax is used as the wax, it is not limited thereto, an animal wax such as beeswax and whale wax and a vegetable was such as a Japan wax may be used, or various mixtures of waxes may be used.

When the hands and feet are soaked in the warm molten bathing agent, a film of wax is formed on the soaked portion, thereby the hands and feet are heated and kept warm. A large number of meridian points distributed on the hands and feet are led to various parts of the body through meridians, thus when the hands and feet are heated and warmed by the warm molten bathing agent consisting mainly of the wax, the whole body is warmed by the thermal reaction of the meridians.

In the bathing agent, more than 1% by weight of minerals such as germanium, iron, magnesium, calcium and the like are contained, which are ionized in the warm molten liquid. The ions are absorbed into the body from the gaps between the nails and serves to warm the body further by the same function as the minerals.

Figure 4:
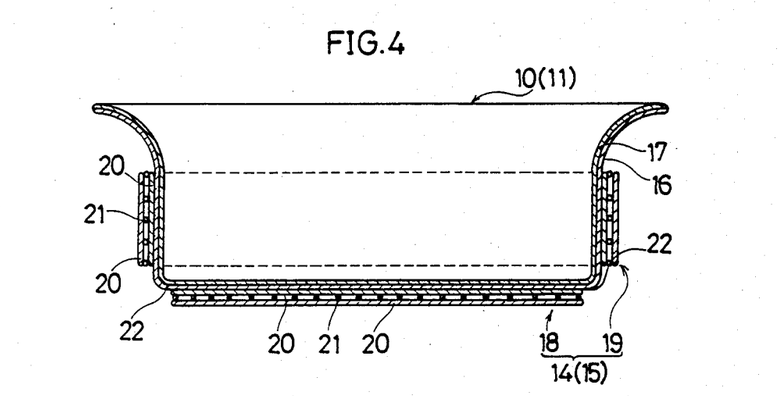
FIG. 4 is a vertical sectional view of a container taken along the line B—B of FIG. 3.

Each container 10, 11 in the upper and lower baths 4, 5 are, as shown in FIG. 4, is formed with a corrosion and acidresisting layer 17 on the inner surface of a stainless base material 16. The layer 17 is designed to protect the inner surface of the container against acid sweat and secretions secreted from the body, for example, if the layer 17 is formed of a silicone rubber, epoxy resin and the like, it is not only resistant to corrosion, but since it is flexible to thermal expansion of the base material 16, thermal deformation and failure of the container can be avoided.

Figure 3:
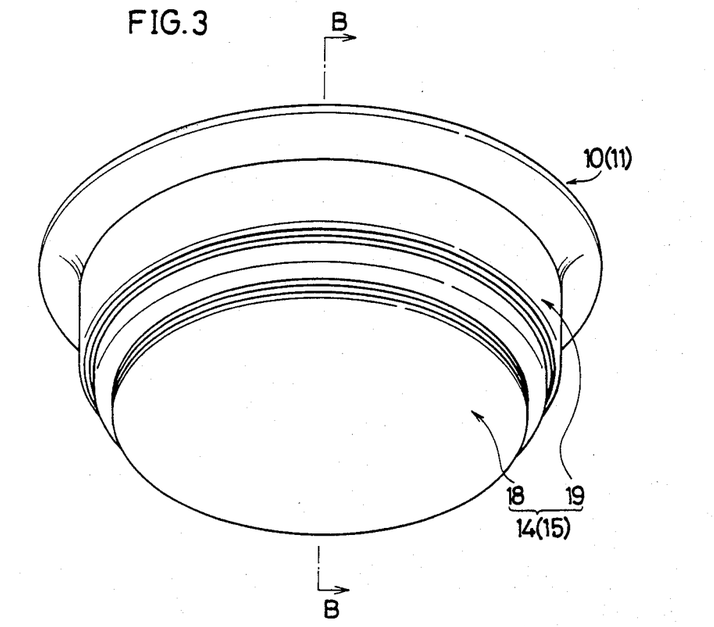
FIG. 3 is a perspective view of a container looking from below.

Though is has been described already that the heating portions 14, 15 are disposed respectively in the upper and lower baths 4, 5, in case of the present invention, each heating portion 14, 15 comprises a first heating portion 18 and a second heating portion 19, the former being disposed equivalently on the bottom of each container 10, 11 and the latter being disposed on the periphery thereof. Each heating portion 18, 19 is, as shown in FIGS. 3 and 4, formed with a face heater comprising a heating wire 21 such as a nickrome wire disposed between fireproof insulating sheets 20, 20 consisting of a silicone rubber and the like. The first heating portion 18 is arranged generally throughout the bottom of the containers 10, 11, and the second heating portion 19 is arranged entirely around the straight periphery of the containers 10, 11. The heating wire 21 of the first heating portion 18 is distributed concentrically and is formed to heat a corner portion 22 located between the heating portions 18, 19 effectively by increasing the distributed density of the outer periphery as compared to the other portions.

In each container 10, 11 of the upper and lower baths 4, 5, an abutting member 23 for destroying a film of wax formed on the surface of the hands and feet is arranged when necessary.

That is, when the hands and feet soaked in the warm molten bathing agent are pulled out, the bathing solvent adhered thereto is gelatinized to form a film of wax due to the lower temperature. When the hands and feet covered with the wax film are soaked again in the warm molten bathing agent, since the skin is protected by the wax film, the thermal stimulus applied to the skin is reduced as compared with the first soaking. If the wax film is destroyed at this state, the warm molten bathing agent flows into the destroyed portion, resulting in a strong thermal stimulus to the skin and an effect as good as moxibustion can be obtained.

Figure 5:
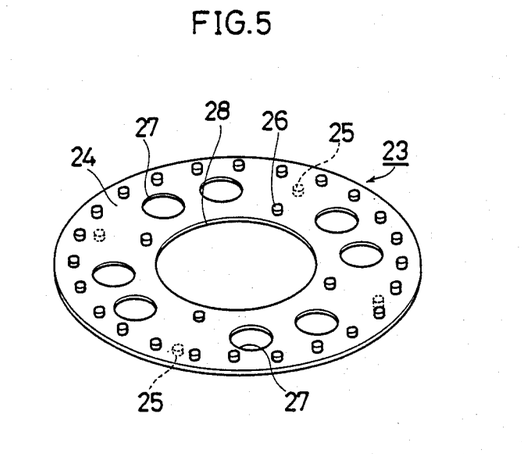
FIG. 5 is a perspective view of an abutting member used in a warm bath for hands and feet of the present invention.

The abutting member 23 is used to destroy the wax film and, for example, as shown in FIG. 5, formed with an annular plate 24 made of a heat-resisting resin having a circular hole 28 in the center. On the annular plate 24, a short leg piece 25 and a plurality of projections 26 are projected respectively on the lower surface and the upper surface thereof, and holes 27 for accelerating convection of the bathing agent together with the center circular hole 28, are open suitably in the plate.

Figure 6:
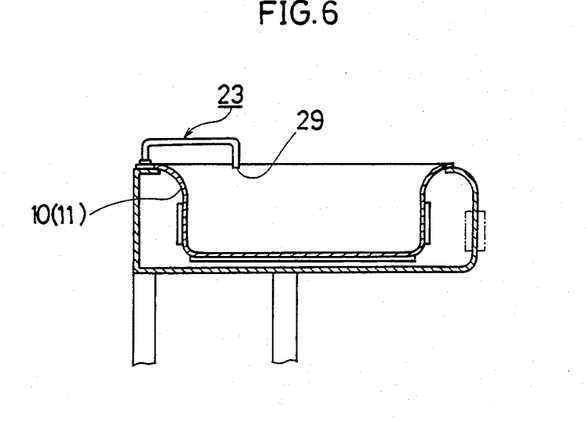
FIG. 6 is a sectional view of a bath showing another embodiment of an abutting member.

The abutting member 23 is constructed not only in such a manner as shown in the embodiment of FIG. 5, which is a submerged type in that it is placed in the bottom of the bath, but is may be also formed as shown, for example, in FIG. 6 to project a bar body in the upper opening of the containers 10, 11. In the case of this embodiment, the wax film can be readily destroyed partly by pressing it against the tip 29 facing downwardly.

In the upper and lower baths 4, 5, heat sensors 30, 31 for detecting the temperature of the warm molten bathing agent in the containers 10, 11 are provided. Responding to the result detected by the heat sensors 30, 31, a temperature control 32 (FIG. 7) to be described later is adapted to control the operation of the heaters 14, 15.

The heat sensors 30, 31 shown in the drawing, are constructed in such a manner that an electric cord (not shown) is inserted through a flexible pipe 33 and provided at its tip with a thermister 34, 35, a heat sensing element, which is immersed in the warm molten bathing agent in each container 10, 11 by bending the pipe downwardly.

Figure 7:
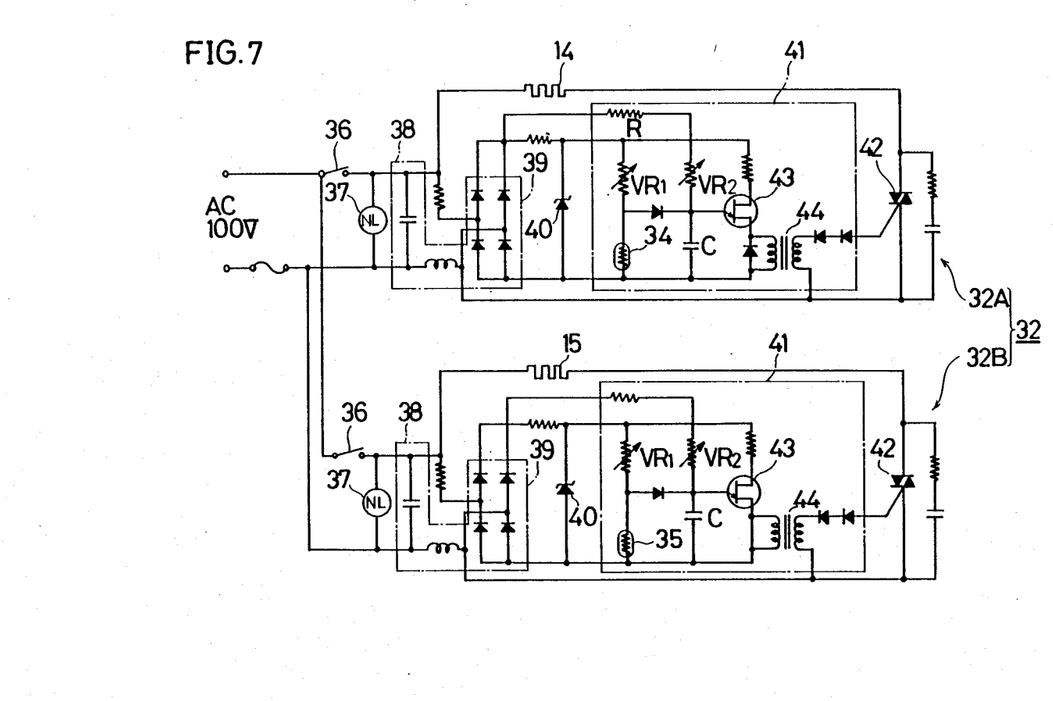
FIG. 7 is an electrical circuit diagram showing a circuit configuration of a temperature control used in a warm bath for hands and feet of the present invention.

FIG. 7 shows a circuit configuration of the temperature control 32. The temperature control 32 shown in the drawing comprises a temperature adjusting circuit of a phase control type, and provided with a first control 32A for controlling the heater 14 of the upper bath 4, and a second control 32B for controlling the heater 15 of the lower bath 5.

The first and second controls 32A, 32B are of an exactly identical construction, therefore, only the first control 32A will be described and that for the second control 32B will be omitted by giving the same reference characters to corresponding parts.

The first control 32A comprises a power switch 36, a neon lamp 37, a noise filter 38, a full-wave rectification circuit 39, a zener diode 40, a trigger circuit 41 and a triac 42, wherein the trigger circuit 41 includes the thermister 34, a resistor R, volume resistors $VR_1$, $VR_2$, a capacitor C, a unijunction transistor 42 (hereinafter referred to as "UJT") and a transformer 44. Circuit configuration members forming the temperature control 32 are incorporated on a printed circuit board and contained in the body 8 of the upper bath 4.

In the first control 32A of the above circuit configuration, to the UJT43 of the trigger circuit 41, trapezoidal wave voltage produced by clamping the full-wave rectification voltage by the zener diode 40 is applied as the driving voltage. The capacitor C in the trigger circuit 41 is charged to a pedestal voltage determined rapidly in the beginning of each half cycle of the trapezoidal wave voltage by a partial pressure of the resistance value of the temperature adjusting volume resistor $VR_1$ and thermister 34, and simultaneously, a charging wave form of $(R + RV_1).C$ determined by the resistor R, volume resistor $VR_1$ and capacitor C is superposed to the pedestal voltage. When the superposed voltage reaches the trigger level of the UJT43, the capacitor C is discharged and the pulse is given to a gate of the triac 42, which is then triggered at a certain conduction angle to supply power to the heater 14.

If the temperature of the warm molten bathing agent in the container 10 drops, which is detected by the thermister 34 and the pedestal voltage is raised to reduce the voltage difference between the trigger level. Thus, the capacitor voltage reaches the trigger level quicker within the cycle and the trigger pulse moves in a direction to widen the conduction angle of the triac 42 and larger power is supplied to the heater 14.

When the temperature of the warm molten bathing agent is increased by heating operation of the heater 14, the above operation is conducted reversely, thus the warm molten bathing agent is automatically adjusted to the prescribed temperature.

INDUSTRIAL APPLICATION

When using a warm bath 1 in accordance with the present invention, after filling each container 10, 11 of upper and lower baths 4, 5 with a bathing agent, heaters 14, 15 are operated to warm and molten the bathing agent. In this case, a volume resistor $VR_1$ of a temperature control 32 is suitably adjusted beforehand by a temperature adjusting knob on a control panel 12 so as to bring the warm molten bathing agent temperature at 47°–55° C., preferably around 52° C.

Since each heater 14, 15 comprises first and second heaters 18, 19 and the bottom of containers 10, 11 is heated by the first heater 18 and the periphery thereof is heated by the second heater 19, the whole containers 10, 11 are heated uniformly.

Thus, even if convection of the bathing agent does not take place sufficiently due to its viscosity, the temperature of the bathing agent is maintained evenly at all positions in the container, and the temperature is controlled precisely by the temperature control 32.

A subject is seated on a chair 3 and his hands and feet are soaked respectively in the upper and lower baths 4, 5 to conduct partial bathing. When the hands and feet are warmed, a body warming operation as good as body bathing by hot spring therapy can be obtained due to the thermal reaction of the meridians, and moxibustion operation is applied simultaneously to the body studded with the meridian points.

Moreover, in this case, though acid sweat and secretions are secreted from the body into the containers 10, 11 into which the hands and feet are soaked, since the inner surface of each container 10, 11 is coated with a corrosion-resisting layer 17, they are free from any corrosion.

EXPERIMENT

A clinical experiment was conducted with 48 persons consisting of 23 males and 25 females, using a warm bath in accordance with the present invention. The clinical experiment was carried out first with each subject in such a manner that subjective symptoms of fatigue, improper blood circulation languid feeling, stiffness, neuralgia or muscular pain, appetite, gastroenteric condition and evacuation were interrogated, and thereafter, the prescribed content of the experiment was performed, then after the experiment, the same interrogation was made again to check the degree of restoration of the subjective symptoms.

The content of the experiment is to perform partial bathing of the hands and feet continuously for two weeks, except Sunday, using the warm bath of the present invention. The bathing agent temperature was kept at 54° C. and 12 bathings of 30 minutes each daily were counted as one treatment period.

In the interrogation made after the experiment, as criteria for determining the treatment result, "very effective" indicates a complete or practical recovery, "effective" shows a tolerable recovery, "little effective" means a little improvement, "not certain" designates an uncertain improvement and "not effective" indicates an ineffective result.

Based upon the interrogation, the clinical results were summarized in the following table.

According to the table, if criteria of "very effective", "effective" and "little effective" are counted as effective, all subjective symptoms show the effective clinical results.

| Subjective Symptoms | Criteria — Effectiveness factor % obtained by counting "Very effective", "Effective" and "Little effective" as effective. |
|---|---|
| Fatigue | 88.89 |
| Improper blood circulation and sensitive to cold of legs and waist | 95.00 |
| Languid Feeling | 86.49 |
| Stiffness | 83.33 |
| Neuralgia or Muscular Pain | 84.38 |
| Appetite | 87.10 |
| Gastroenteric Condition | 80.65 |

| | Criteria |
|---|---|
| Subjective Symptoms | Effectiveness factor % obtained by counting "Very effective", "Effective" and "Little effective" as effective. |
| Evacuation | 80.00 |

What is claimed is:

1. A warm bath for simultaneously soaking and warming the hands and feet in a bathing agent consisting mainly of wax, the combination comprising an upper container overlying a lower container with each containing said bathing agent, connecting means connecting said upper container to said lower container, said upper and lower container each having a bottom wall and a peripheral side wall which is generally upright, said bottom wall and peripheral side wall of each container each comprising a base structure and an inner layer on said base structure, said inner layer being made of a corrosion-resistant material, abutting means on at least one of said containers for facilitating removal of wax from a person's body part, said at least one container having a top opening, said abutting means comprising a bar member mounted on said base structure and extending over said top opening of said container, said bar member having an L-shaped configuration including a first horizontal leg and a downward depending vertical leg, said vertical leg having a terminating end operable to remove said wax from a person's body parts, said base structure having a bottom outer surface juxtaposed to said bottom wall and a side outer surface juxtaposed to said side wall, first electric heater means on said bottom outer surface, second electric heater means on said side outer surface, a temperature sensor means for detecting the temperature of said bathing agent in each of said containers, and temperature control means operably connected between said temperature sensor means and said first and second electric heater means for controlling the temperature of said bathing agent in each of said containers, whereby the entire volume of the bathing agent in each of said upper and lower containers is uniformly heated by said first and second electric heater means and the temperature of the bathing agent in said upper and lower containers is maintained substantially even at all locations in the respective container by said first and second electric heater means.

2. A warm bath according to claim 9 wherein said heater wire of said first electric heater means is distributed concentrically at a position underlying said bottom wall, said heater wire of said second electric heater means extending entirely around said upright peripheral side wall, whereby substantially the entire bottom wall and side wall of each container is headed by said first and second electric heater means.

3. A war bath according to claim 9 wherein said heater wire comprises nickrome wire and said sheets comprise silicone rubber.

4. A warm bath according to claim 1 wherein said corrosiveresistant material of said inner layer comprises a flexible material which is expandable upon thermal expansion of said base structure.

5. A warm bath according to claim 4 wherein said corrosiveresistant material of said inner layer is selected from the group consisting of silicone rubber and expoxy resin.

6. A warm bath according to claim 8 wherein said annular plate is made of a heat-resisting resin material.

7. A warm bath according to claim 8 wherein said opening means comprises a central opening and a plurality of outer openings disposed about said central opening.

8. A warm bath for simultaneously soaking and warming the hands and feet in a bathing agent consisting mainly of wax, the combination comprising an upper container overlying a lower container with each containing said bathing agent, connecting means connecting said upper container to said lower container, said upper and lower container each having a bottom wall and a peripheral side wall which is generally upright, said bottom wall and peripheral side wall of each container each comprising a base structure and an inner layer on said base structure, said inner layer being made of a corrosion-resistant material, said base structure having a bottom outer surface juxtaposed to said bottom wall and a side outer surface juxtaposed to said side wall, abutting means on at least one of said containers for facilitating removal of wax from a person's body part, said abutting means comprising an annular plate having an upper and a lower generally flat surface, a plurality of generally upright projections extending from said upper surface, a plurality of downwardly depending projections extending from said lower surface, said downwardly depending projections having bottom terminating ends abutting said bottom wall of said container to thereby provide a space between said bottom wall of said container and said lower surface of said abutting member, firs electric heater means on said bottom outer surface, second electric heater means on said side outer surface, a temperature sensor means for detecting the temperature of said bathing agent in each of said containers, and temperature control means operably connected between said temperature sensor means and said first and second electric heater means for controlling the temperature of said bathing agent in each of said containers, whereby the entire volume of the bathing agent in each of said upper and lower containers is uniformly heated by said first and second electric heater means and the temperature of the bathing agent in said upper and lower containers is maintained substantially even at all locations in the respective container by said first and second electric heater means, and opening means in said annular plate such that said bathing agent passes through said opening means to facilitate movement and circulation of said bathing agent through said annular plate during heating of said bathing agent by said first and second heater means.

9. A warm bath for simultaneously soaking and warming the hands and feet in a bathing agent consisting mainly of wax, the combination comprising an upper container and a lower container with each containing said bathing agent, connecting means connecting said upper container to said lower container, said upper and lower container each having a bottom wall and a peripheral side wall which is generally upright, said bottom wall and peripheral side wall of each container each comprising a base structure and an inner layer on said base structure, said inner layer being made of a corrosion-resistant material, said base structure having a bottom outer surface juxtaposed to said bottom wall and a side outer surface juxtaposed to said side wall, first electric heater means on said bottom outer surface, second electric heater means on said side outer surface, each of said electric heater means comprising a heater wire sandwiched between fireproof insulating sheets, one of said sheets of said first electric heater means being fixed to said bottom outer surface of said base structure, one of said sheets of said second heater means being fixed to said side outer surface of said base structure, each of said containers having a corner part joining the respective bottom wall and peripheral side wall, said heater wire of said first electric heater means having a first section of one distribution density at a concentric center portion of said bottom wall and a second section of another distribution density at an outer annular portion surrounding said central portion, said second section extending substantially to said corner part, said other distribution density being greater than said one distribution density to thereby provide for heating of the bathing agent disposed at said corner part, a temperature sensor means for detecting the temperature of said bathing agent in each of said containers, and temperature control means operably connected between said temperature sensor means and said first and second electric heater means for controlling the temperature of said bathing agent in each of said containers, whereby the entire volume of the bathing agent in each of said upper and lower containers is uniformly heated by said first and second electric heater means and the temperature of the bathing agent in said upper and lower containers is maintained substantially even at all locations in the respective container by said first and second electric heater means.

* * * * *